United States Patent [19]

Chorvat et al.

[11] Patent Number: 4,554,353
[45] Date of Patent: Nov. 19, 1985

[54] 2,5-PYRROLIDINEDIONE DERIVATIVES USEFUL AS ANTIARRHYTHMIC AGENTS

[75] Inventors: Robert J. Chorvat, Arlington Heights; Bipinchandra N. Desai, Vernon Hills, both of Ill.

[73] Assignee: G. D. Searle & Co., Skokie, Ill.

[21] Appl. No.: 637,633

[22] Filed: Aug. 3, 1984

[51] Int. Cl.$^4$ .................. C07D 403/06; C07D 207/40
[52] U.S. Cl. ..................................... 546/208; 548/546
[58] Field of Search ........................ 546/208; 548/546

[56] References Cited

U.S. PATENT DOCUMENTS 2,666,060  1/1954  Sury et al. ........................... 546/208

Primary Examiner—Robert T. Bond
Attorney, Agent, or Firm—John J. McDonnell

[57] ABSTRACT

This invention encompasses compounds of the formula

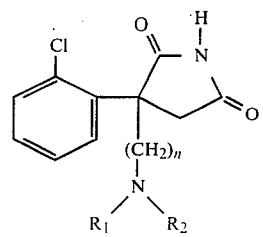

and pharmaceutically acceptable acid addition salts thereof wherein n is 2 or 3 and $R_1$ and $R_2$ are n-propyl, isopropyl, or $R_1$ and $R_2$ together with N form a 2,6-dimethyl-1-piperidinyl group. The compounds of this invention are useful as antiarrhythmic agents.

4 Claims, No Drawings

2,5-PYRROLIDINEDIONE DERIVATIVES USEFUL AS ANTIARRHYTHMIC AGENTS

BRIEF DESCRIPTION OF THE INVENTION

This invention encompasses compounds of the formula I

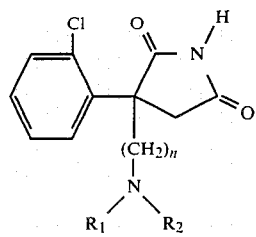

and the pharmaceutically acceptacle acid addition salts thereof wherein n is 2 or 3 and $R_1$ and $R_2$ are n-propyl, isopropyl, or $R_1$ and $R_2$ together with N form a 2,6-dimethyl-1-piperidinyl group. The compounds of this invention are useful as antiarrhythmic agents which have low anticholinergic side effects. This invention also encompasses methods of using these compounds for treating cardiac arrhythmia as well as the closely related compounds described in the examples.

DETAILED DESCRIPTION OF THE INVENTION

U.S. Pat. No. 2,666,060 discloses compounds of the formula II

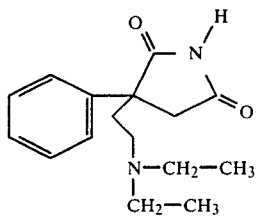

and teaches these compounds as intermediates to ganglionic blocking agents. J. Pharm. Sciences 59, 1028, (1970) discloses the N-methyl derivatives as an anticonvulsant agent. Helv. Chim. Acta. 35, 1235 (1952) discloses compounds of the formula

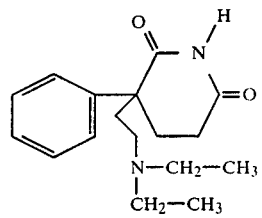

It has been discovered that compounds of the formula

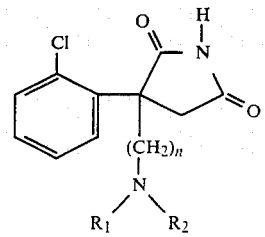

and the pharmaceutically acceptable acid addition salts thereof where n is 2 or 3 and $R_1$ and $R_2$ is n-propyl, isopropyl or $R_1$ and $R_2$ together with N form 2,6-dimethyl-1-piperidinyl group are potent antiarrhythmic agents with low anticholinergic activity. This activity is illustrated by Table I.

|  | Harris Dog Efficacy | $IC_{50}$ Muscarinic Receptor Binding Assay |
|---|---|---|
| Example 4 | 2.8 MPK | 0.3 $\mu$M |
| Example 6 | 1.3 MPK | 0.47 $\mu$M |
| Formula II (Prior Art) | 2 MPK | 0.02 $\mu$M |
| Example 14 | 1 MPK | 3.6 $\mu$M |
| Example 2 | 10 MPK | 0.14 $\mu$M |

The potential anticholinergic side effects were determined by measuring the compound's ability to bind to muscarine receptors in a rat brain homogenate. Male Charles River CD rats weighing 200–250 g were sacrificed by cervical dislocation, the brains removed and the cerebellum discarded. The remaining tissue was homogenized in 30 volumes of 0.32 sucrose with a teflon-glass homogenizer. The crude homogenate was centrifuged at 4° C. for 10 minutes at 100 $\times$g. The supernatant friction was rehomogenized and used without further purification as the membrane receptor preparation for the assay. Each assay tube contained 50 $\mu$l of the membrane preparation and 20 $\mu$l of the radioligand, $^3$H-quinuclidinyl benzylate 30.2 Ci/mmole, ($^3$H—QNB). Test compounds were suspended in 100% EtOH, diluted further in 0.05M sodium-potassium phosphate buffer (pH 7.4) to appropriate concentrations, and 20 $\mu$l of this solution was added to tubes containing the $^3$H—QNB preparation. Final volume of 2.0 ml per tube was achieved by adding appropriate volumes of 0.05M sodium-potassium phosphate buffer (pH 7.4). Each drug concentration and control tube was assayed in triplicate.

The reaction was initiated by addition of 0.15 nM of $^3$H—QNB and incubating the tubes in a reciprocating water bath for 1 hour at 25° C. The assay was terminated by addition of 4 ml of ice-cold sodium-potassium phosphate buffer, samples filtered over Whatman GF/B filters under reduced pressure, and the filters rinsed two more times with 4 ml aliquots of ice-cold buffer. Filters were warmed at 50° C. for 30 minutes to remove all moisture. The samples were diluted to 10 ml and counted using a liquid scintillation counter.

Total binding to the receptor was determined from samples containing only $^3$H—QNB. Non-specific binding was measured as residual binding in the presence of $10^{-5}$M atropine sulfate. Total binding minus non-specific binding (NSB) yielded the specific binding of a compound. The $IC_{50}$'s were determined from log-logit plots and represent that concentration of test compound which inhibits specific $^3$N—QNB binding by 50%.

The antiarrhythmic activity of these compounds is illustrated by the following test.

Ventricular arrhythmia is induced by a 2-stage ligation of the anterior descending branch of the left coronary artery in each of two or more unanesthetized dogs. The test compound is administered intravenously at 5 mpk doses to a maximum dose of 20 mpk. A compound is rated active if it produces at least a 25% reduction in ectopic beats for a period of at least 10 minutes in half or more of the dogs tested. The average minimal effective dose is determined for each active compound.

Antiarrhythmic agents effective in man such as quinidine, procainamide, and Norpace ® are active in this test.

Those compounds found active to the extent of 75–100% reduction in ventricular arrhythmia or toxic at 5 mpk in the above test are tested by administering 1 mpk doses at five minute intervals up to a total of 6 mpk total dose. A compound is rated active if it produces at least a 25% reduction in ectopic beats for a period of at least 10 minutes in half or more of the dogs tested.

Scheme I illustrates the preparation of compounds of this invention wherein $R_1$, $R_2$ and n are as previously defined and the examples more fully set out the details of the invention.

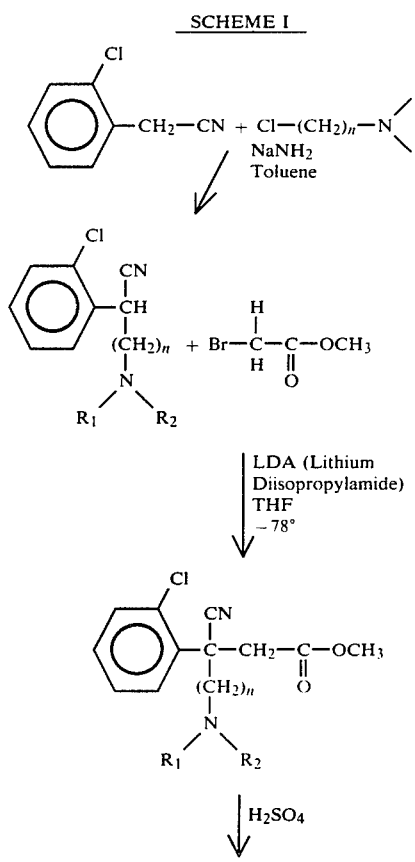

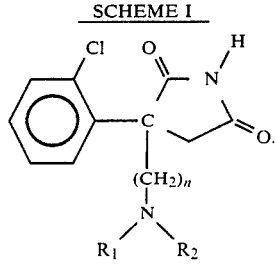

Compounds of this invention are formulated into conventional dosage forms such as tablets, capsules, and injectibles.

Pharmaceutically acceptable acid addition salts are derived from the base of formula I and a mineral and organic acid such as sulfuric, hydrochloric, hydrobromic, hydroiodic, phosphoric, nitric, sufinic, sulfonic, toluenesulfonic, acetic, benzoic, furmaric, succinic acid and the like.

The hereinafter set out examples are intended to illustrate the invention and not limit it in spirit or scope.

EXAMPLE 1

64 ml of 1.0 molar n-butyllithium is added to 16 ml of diisopropylamine in 200 ml of freshly distilled tetrahydrofuran (THF) at 0° C. for 15 minutes. The solution is then cooled to −50° C., and 24.1 g of α-[2-bis-(1-methylethyl)amino]ethylphenylacetonitrile in 50 ml of THF is added at −50° C. After stirring the reaction mixture for 15 min., 10.5 ml of methylbromoacetate in 50 ml of THF is added and the reaction mixture is allowed to warm to 0° C. After quenching with water and extracting with 2×100 ml portions of ether, the extracts are washed with water, dried over anhydrous magnesium sulfate and the solvent is removed under reduced pressure. The resultant crude oil is taken up in 200 ml of 10% HCl solution. The acidic solution is washed once with ether before basifying with 50% sodium hydroxide solution and extracting 3× with 50 ml portions of ether. The ether extracts are dried over magnesium sulfate and the solvent is removed under reduced pressure to provide 26.0 g of crude product which is distilled at 205° C. (0.3 mm) to afford 20.5 g of methyl β-[2-[bis-(1-methylethyl)amino]ethyl]-β-cyano benzenepropanoate.

EXAMPLE 2

A solution of 10.0 g of the material prepared in Example 1 and 20 ml of sulfuric acid is heated on the steam bath for 15 minutes, cooled to room temperature, and poured onto ice water. The acidic solution is extracted 2× with 100 ml portions of ethylacetate before basifying with 50% NaOH solution and extracting with 3 portions of ethyl acetate. The extracts are washed with water, dried over anhydrous magnesium sulfate, and the solvent is removed by evaporation under reduced pressure. The resultant crude product is crystallized from the mixture of ether and hexane to provide 4.4 g of 3-[2-[bis(1-methylethyl)amino]ethyl]-3-phenyl-2,5-pyrrolidinedione having the formula

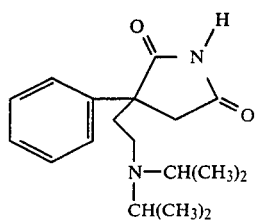

Calc. for $C_{18}H_{26}N_2O_2$: C, 71.49; H, 8.67; N, 9.24. Found: C, 71.39; H, 8.37; N, 9.19.

EXAMPLE 3

Following the procedure described in Example 1 and replacing α-[2-bis(1-methylethyl)amino]ethyl phenylacetonitrile with α-[2-bis(1-methylethyl)amino]ethyl-2-chlorophenylacetonitrile provides methyl β-[2-[bis(1-methylethyl)amino]ethyl]-2-chloro-β-cyanobenzenepropanoate having the formula

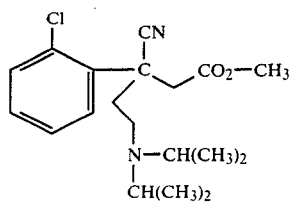

Calc. for $C_{19}H_{27}N_2O_2Cl$: C, 65.04; H, 7.76; N, 7.98. Found: C, 65.19; H, 7.85; N, 8.03. B.P.: 185°–190° C. (0.3 mm)

EXAMPLE 4

Following the procedure described in Example 2 and substituting the material prepared in Example 1 with the material prepared in Example 3 provides 3-[2-[bis(1-methylethyl)-amino]ethyl]-3-(2-chlorophenyl)-2,5-pyrrolidinedione having the formula

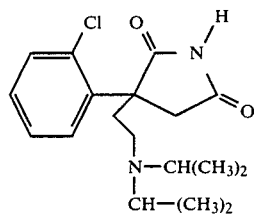

Calc. for $C_{18}H_{25}N_2O_2Cl$: C, 64.18; H, 7.48; N, 8.32. Found: C, 64.15; H, 7.50; N, 8.37. M.P.: 116.5°–119° C.

EXAMPLE 5

Following the procedure described in Example 1 and substituting α-[2-bis(1-methylethyl)amino]ethyl phenylacetonitrile with α-[2-(2,6-dimethyl-1-piperidinyl)]-2-chlorophenylacetonitrile provides methyl 2-chloro-β-cyano-β-[2-(2,6-dimethyl-1-piperidinyl)ethyl]benzenepropanoate having the formula

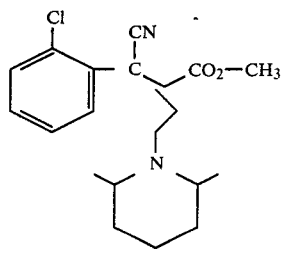

Calc. for $C_{20}H_{27}N_2O_2Cl$: C, 66.19; H, 7.50; N, 7.71. Found: C, 65.81; H, 7.46; N, 7.58.

EXAMPLE 6

Following the procedure described in Example 2 and starting with the material prepared in Example 5 provides 3-(2-chlorophenyl)-3-[2-(2,6-dimethyl-1-piperidinyl)ethyl]-2,5-pyrrolidinedione having the formula

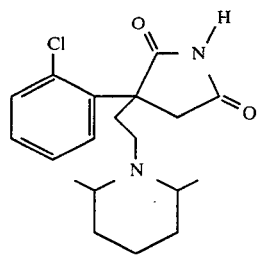

Calc. for $C_{19}H_{25}N_2O_2Cl$: C, 65.40; H, 7.22; N, 8.02. Found: C, 65.11; H, 7.23; N, 7.91.

EXAMPLE 7

Following the procedure described in Example 1 and substituting α-[2-bis(1-methylethyl)amino]ethyl phenylacetonitrile with α-[2-(2,6-dimethyl-1-piperidinyl)]ethyl-2,4-dichlorophenylacetonitrile provides methyl β-cyano-2,4-dichloro-β-[2-(2,6-dimethyl-1-piperidinyl)ethyl]benzenepropanoate having the formula

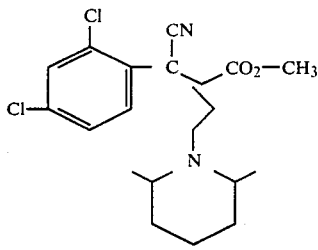

NMR: ($^1$H, δ, CDCl$_3$, 60 MH$_z$); 3.53 (3H, s, —CO$_2$CH$_3$), 1.06 (6H, m, —N—C—CH$_3$)

EXAMPLE 8

Following the procedure described in Example 2 and starting with material prepared in Example 7 provides 3-(2,4-dichlorophenyl)-3-[2-(2,6-dimethyl-1-piperidinyl)ethyl]-2,5-pyrrolidinedione having the formula

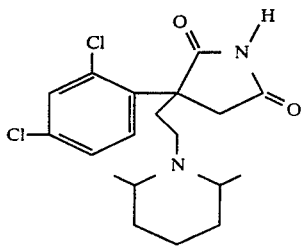

Calc. for $C_{19}H_{24}N_2O_2Cl$: C, 59.53; H, 6.30; N, 7.30. Found: C, 59.50; H, 6.54; N, 7.04.

EXAMPLE 9

Following the procedure described in Example 1 and substituting methylbromoacetate with methyl-2-bromo-propionate yields methyl β-[2-bis(1-methylethyl)amino]ethyl]-2-chloro-β-cyano-α-methylbenzenepropanoate having the formula

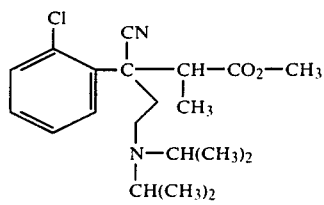

NMR: ($^1$H, δ CDCl$_3$, 60 MH$_z$); 3.7 (3H, S, —CO$_2$CH$_3$), 0.96 (12H, d, —N—C—CH$_3$)

EXAMPLE 10

Following the procedure described in Example 2 and starting with material prepared in Example 9 provides a mixture of diastero isomeric α-methylpyrrolidinediones. Chromatographic separation provides individual racemates of 3-[2-bis(1-methylethyl)amino]ethyl]-3-(2-chlorophenyl)-4-methyl-2,5-pyrrolidinedione having formula)

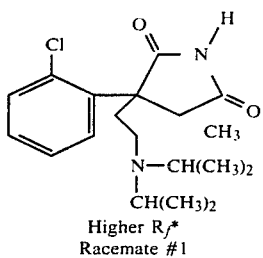
Higher R$_f$*
Racemate #1

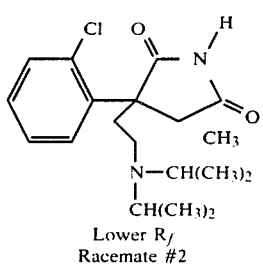
Lower R$_f$
Racemate #2

*TLC system to determine relative Rf's. 70% by volume cyclohexane, 28% ethanol, 2% NH$_4$OH on silica gel.

For Racemate #1

Calc. for $C_{19}H_{27}N_2O_2Cl$: C, 65.03; H, 7.76; N, 7.98. Found: C, 65.06; H, 7.82; N, 7.89.

For Racemate #2
Calc. for $C_{19}H_{27}N_2O_2Cl$: C, 65.03; H, 7.76; N, 7.98. Found: C, 65.40; H, 7.86; N, 8.04.

EXAMPLE 11

9.5 ml of 1.6M n-butyllithium in hexane is added to 2.3 ml of diisopropylamine in 50 ml of freshly distilled THF at 0° C. under nitrogen atmosphere. The mixture is stirred at 0° C. for 10 minutes, cooled to −50° C. and 5.47 g of material prepared in Example 9 is added to the mixture at −50° C. The mixture is stirred at −50° C. for 15 minutes before adding 3.0 ml of methyl iodide. The mixture is then warmed to 0° C. and quenched with water and is extracted 2× with 50 ml portions of ether. The ether extract is washed with water, dried over anhydrous magnesium sulfate. The solvent is removed by evaporation under reduced pressure to provide 3.1 g of methyl β-[2-bis(1-methylethyl)amino]ethyl]-2-chloro-β-cyano-α,α-dimethylbenzenepropanoate having the formula

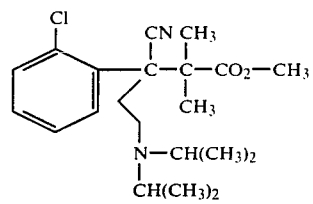

NMR: ($^1$H, δ, CDCl$_3$, 60 MH$_z$); 3.66 (3H, s, —CO$_2$CH$_3$), 1.53 (3H, s, —C—CH$_3$), 1.33 (3H, s, —C—CH$_3$)

EXAMPLE 12

Following the procedure described in Example 2 and starting with material prepared in Example 1 provides 3-[2-bis(1-methylethyl)amino]ethyl-3-(2-chlorophenyl-4,4-dimethyl-2,5-pyrrolidinedione hydrochloride, isolated after treatment of the free base in ether with 6N HCl in dioxane solution, having formula

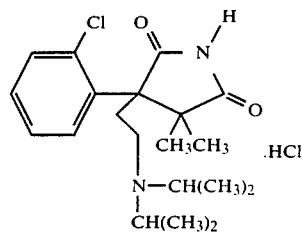

mp: 257°–260° C.

EXAMPLE 13

Following the procedure described in Example 1 and substituting α-[2-bis(1-methylethyl)amino]ethyl phenylacetonitrile with α-[3-(dipropylamino)propyl]-2-chlorophenylacetonitrile provides methyl-2-chloro-β-cyano-β-[3-(dipropylamino)propyl]benzenepropanoate having the formula

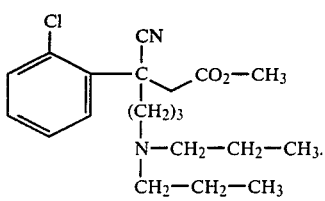

B.P.: 190°-195° C. (0.3 mm)

EXAMPLE 14

Following the procedure described in Example 2 and starting with the material prepared in Example 13 provides 3-(2-chlorophenyl)-3-[3-(di-n-propylamino-propyl]-2,5-pyrrolidinedione having the formula

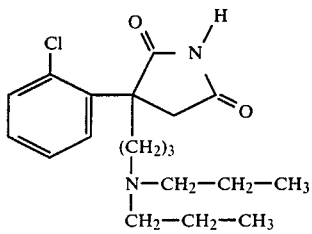

Calc. for $C_{20}H_{29}N_2O_2Cl$: C, 65.82, H, 8.01; N, 7.67. Found: C, 65.72; H, 7.80; N, 7.47.

EXAMPLE 15

Following the procedure described in Example 1 and substituting α-[2-Bis(1-methylethyl)amino]ethyl-phenylacetonitrile with α-[2-bis(2-methylpropyl)amino]ethyl-2-chlorophenylacetonitrile provides methyl-2-chloro-β-cyanobenzenepropanoate having the formula

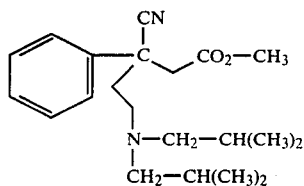

Calc. for $C_{21}H_{31}N_2ClO_2$: C, 66.57; H, 8.24; N, 7.38. Found: C, 66.90; H, 8.27; N, 7.43.

B.P.: 180°-185° C. (0.3 mm)

EXAMPLE 16

Following the procedure described in Example 2 and starting with material prepared in Example 15 provides 3-[2-bis(2-methylpropyl)amino]ethyl]-3-(2-chlorophenyl)-2,5-pyrrolidinedione having the formula

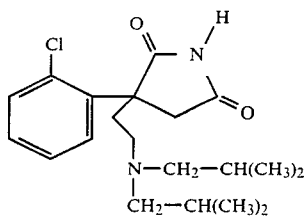

Calc. for $C_{20}H_{29}N_2O_2Cl$: C, 65.82; H, 8.01; N, 7.67. Found: C, 65.73; H, 7.80; N, 7.47.

What is claimed is:

1. A compound of the formula:

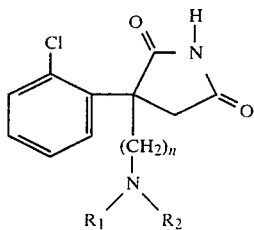

and the pharmaceutically acceptable acid addition salts thereof wherein n is 2 or 3;

and $R_1$ and $R_2$ are n-propyl or isopropyl or $R_1$ and $R_2$ together with the nitrogen form a 2,6 dimethyl-1-piperidinyl group.

2. A compound according to claim 1 which is 3-[2-[bis(1-methylethyl)amino]ethyl]-3-(2-chlorophenyl)-2,5-pyrrolidinedione and the pharmaceutically acceptable acid addition salts thereof.

3. A compound according to claim 1 which is 3-(2-chlorophenyl)-3-[2-(2,6-dimethyl-1-piperidinyl)ethyl]-2,5-pyrrolidinedione and the pharmaceutically acceptable acid addition salts thereof.

4. A compound according to claim 1 which is 3-(2-chlorophenyl)-3-[3-di-n-propylaminopropyl]-2,5-pyrrolidinedione and the pharmaceutically acceptable acid addition salts thereof.

* * * * *